United States Patent [19]
Lindauer

[11] Patent Number: 5,139,864
[45] Date of Patent: Aug. 18, 1992

[54] MULTI-LAYER, MULTI-FUNCTIONAL VOLATILIZABLE SUBSTANCE DELIVERY ARTICLES

[75] Inventor: Jerome I. Lindauer, Hillsdale, N.J.

[73] Assignee: International Flavors & Fragrances Inc., New York, N.Y.

[21] Appl. No.: 805,021

[22] Filed: Nov. 11, 1991

[51] Int. Cl.⁵ .............................................. B32B 3/26
[52] U.S. Cl. ............................... 428/304.4; 428/305.5; 428/316.6; 428/905
[58] Field of Search ............... 428/304.4, 305.5, 316.6, 428/905

[56] References Cited

U.S. PATENT DOCUMENTS

| | | | |
|---|---|---|---|
| 4,429,869 | 1/1984 | Munteanu et al. | 252/522 A |
| 4,440,542 | 4/1984 | Foley | 428/305.5 |
| 4,502,234 | 3/1985 | Schaefer et al. | 428/316.6 |
| 4,521,541 | 6/1985 | Rutherford et al. | 521/79 |

FOREIGN PATENT DOCUMENTS 3128314 5/1991 Japan.
1598449 9/1981 United Kingdom.

Primary Examiner—William J. Van Balen
Attorney, Agent, or Firm—Arthur L. Liberman

[57] ABSTRACT

Described are multi-layer, multi-functional volatilizable substance delivery articles. The articles are constructed in order to deliver, in sequentially-timed fashion, to the environment surrounding the article (e.g., atmosphere, or body of water) different fish feed attractants, repellents, combinations thereof, perfumes having different aroma profiles, insect repellents which repel different insects . . . during the day time hours and during the night time hours, air freshener-insect repellent combinations, perfume-air freshener combinations and the like. The article can be constructed where one of the layers is a gel layer and the matrix layer adjacent thereto is composed of perfume-containing particles which emit a fragrance in a sustained release fashion.

5 Claims, 4 Drawing Sheets

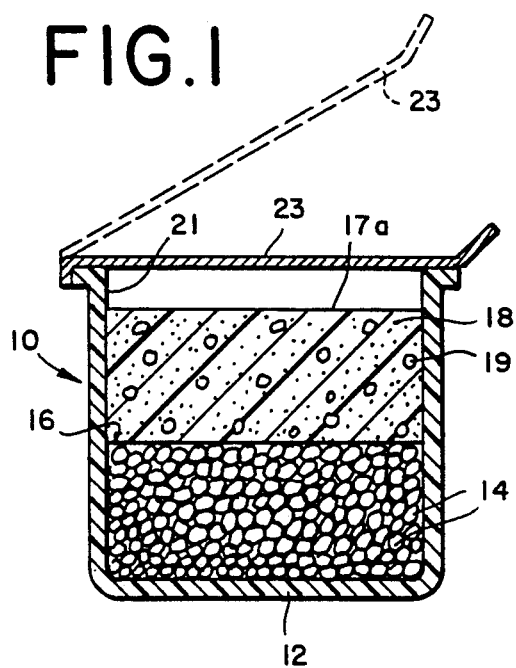
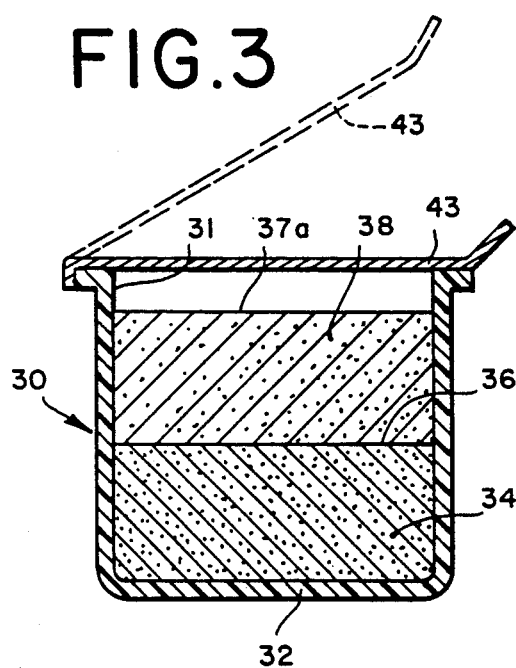
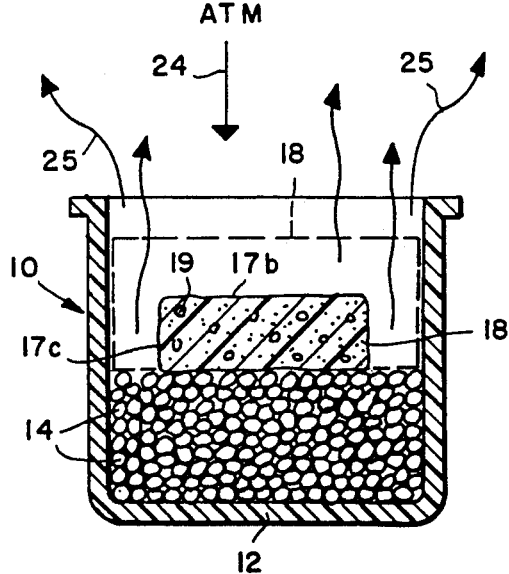
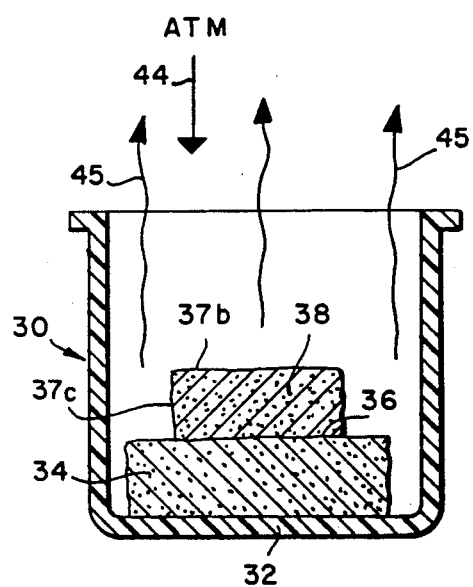

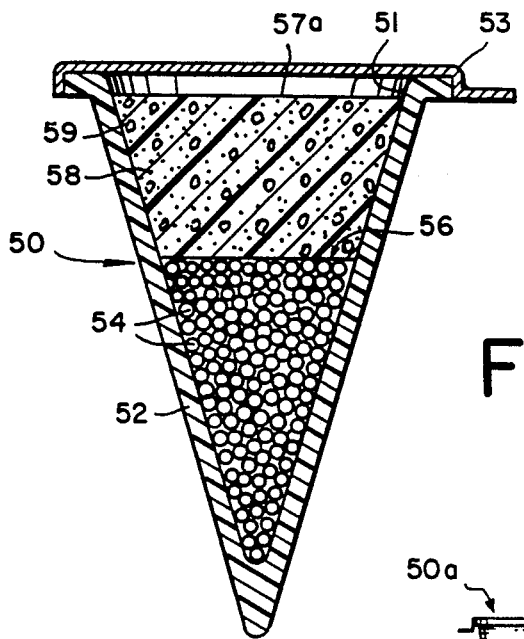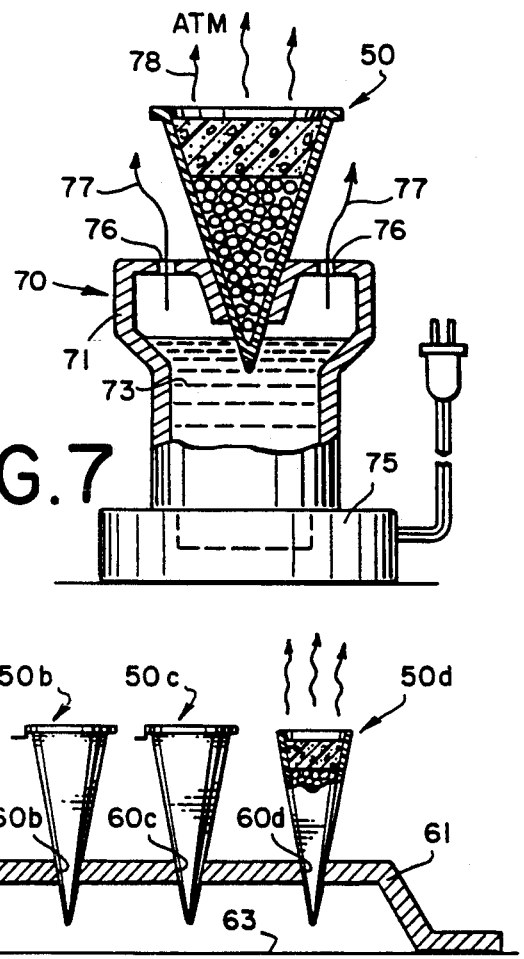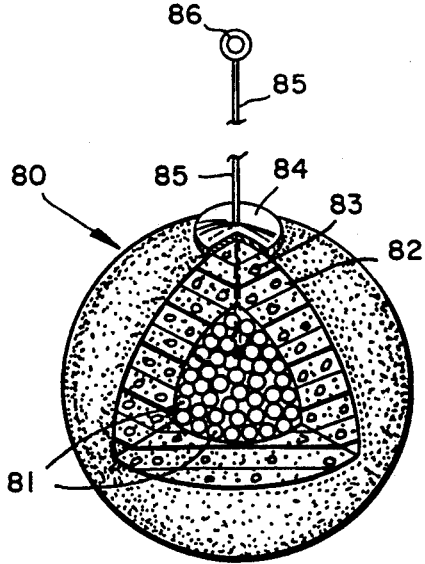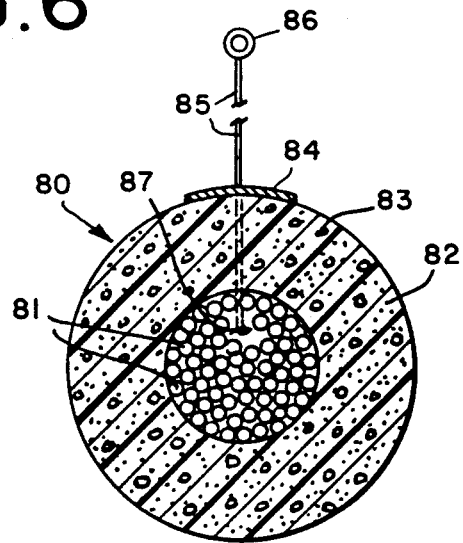

FIG.10
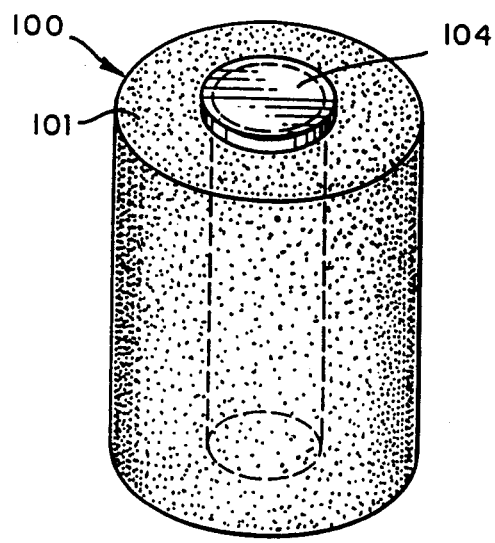
FIG.11
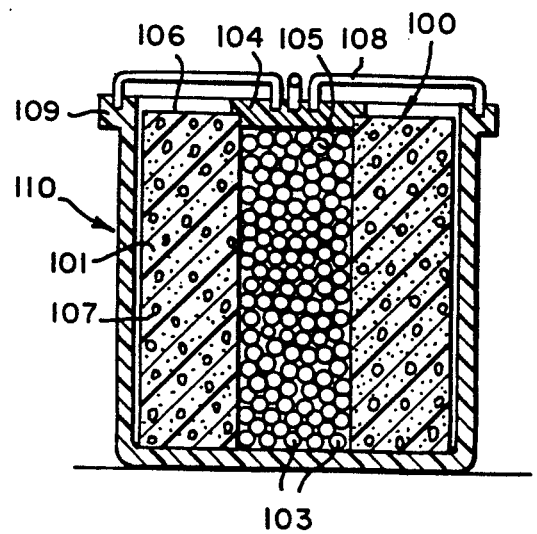
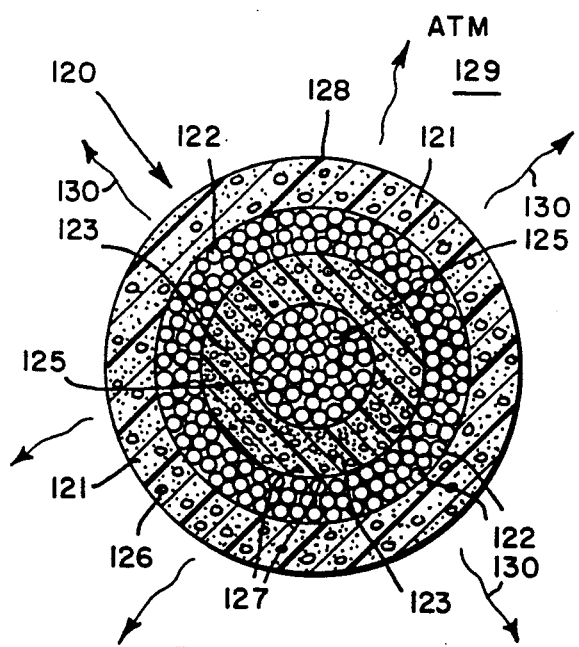
FIG.12
FIG.13
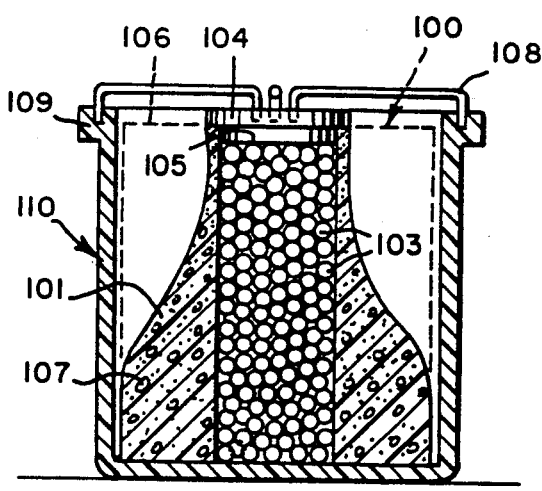

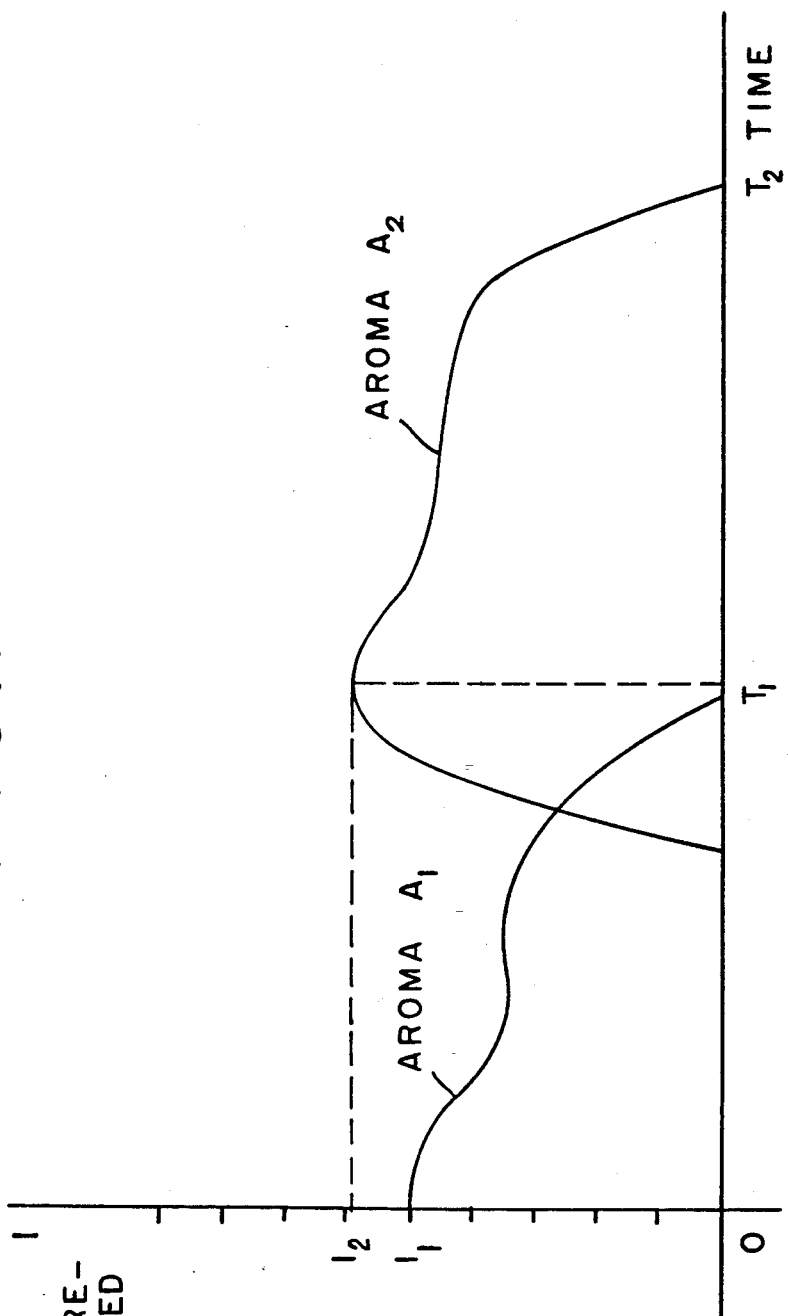

MULTI-LAYER, MULTI-FUNCTIONAL VOLATILIZABLE SUBSTANCE DELIVERY ARTICLES

BACKGROUND OF THE INVENTION

Our invention relates to multi-layer sequentially timed release polyfunctional volatilizable substance delivery articles which comprise a plurality of concentric or coaxial neighboring matrix layers.

There has been considerable work performed relating to volatilizable substances including fragrance substances which have a fragrance impact both initially and over extended periods of time during the consumption of the consumable material in which the volatilizable substance, e.g., fragrance is located. Problems have arisen in attempting to create such fragrance compositions for use with hydro-alcohol compositions of matter such as colognes, wherein part of the fragrance is available for immediate results whereas another part of the fragrance provides the effect gradually over extended periods of time; and further, in different manners in different controllable periods of time. Such problems include the continuous distribution of "initial impact" and "extended release" fragrance over the entire mass of the hydro-alcohol composition of matter (e.g., colognes) as well as commercial manufacture of same.

In U.S. Pat. No. 4,428,869 issued Jan. 31, 1984, hydro alcohol compositions of matter such as colognes are described wherein part of the fragrance is available for immediate results whereas another part of the fragrance provides the effect gradually over extended periods of time; and further, in different manners in different controllable periods of time.

U.S. Pat. No. 3,920,849, describes orally utilizable compositions which may be either chewing gum compositions, chewable medicinal tablets, chewing tobacco or toothpaste having, on oral intake, a high flavor intensity release evenly and uniformly over an extended oral utilization time in the mouth cavity; the orally utilizable compositions containing a non-confined flavor oil, a flavor oil which is physically entrapped in solid particles and a suspending agent such as silica, xanthan gum, ethyl cellulose and hydroxypropyl cellulose; the non-confined flavor oil, the entrapped flavor oil and the suspension agent being premixed prior to addition to either the chewing gum base, the chewing tobacco, the chewable medicinal tablet base, the toothpaste base, the smoking tobacco or the hot beverage.

U.S. Pat. No. 2,886,440 teaches a method of preparing a chewing gum characterized by "extended flavor perception time, true flavor character, and high degree of flavor release comprising the steps of forming a spray-dried emulsion of a volatile, water-immiscible flavoring agent encapsulated within finely divided particles of gelatin, and substantially uniformly distributing said gelatin encapsulated flavoring agent within an all enveloping mass of a chewing gum base".

U.S. Pat. No. 2,886,446 teaches a chewing gum comprising (i) smaller particles of gelatin characterized by faster liberation of flavor and (ii) larger particles of gelatin characterized by slower liberation of flavor, each of the gelatin particles containing dispersed therewithin, in dried emulsion form, discrete micro-droplets of a volatile water-immiscible flavoring agent, and an all-enveloping mass of a chewable gum base within which the particles are substantially uniformaly distributed whereby the flavor is released substantially evenly and uniformly over the extended chewing time.

U.S. Pat. No. 2,886,445 teaches that:

"It is now possible to obtain a flavoring composition, particularly adapted for use in chewing gum which permits attainment of a product characterized by extended flavor perception time, true flavor character, and release of a large proportion of flavoring agent. This flavoring composition comprises finely divided particles of a dried hardened gelatin emulsion containing discrete micro-droplets of a volatile, water-immiscible flavor agent. Preparation of the flavoring composition of this invention may be effected by encapsulating discrete micro-droplets of volatile, water-immiscible flavoring agent within finely divided particles of a dried emulsion of hardened gelatin".

U.S. Pat. No. 2,886,449 teaches:

"A chewing gum containing a flavoring composition characterized by an extended flavor perception time, true flavor character, controlled release of a large portion of flavoring agent, and reduction in amount of flavor oil required (which) may be prepared by the process comprising forming a gelatin-coacervated flavor, and substantially uniformly distributing said gelatin-coacervated flavor within an all-enveloping mass of a chewable gum base. The product chewing gum . . . comprises . . . finely divided particles of coacervated gelatin containing a water-immiscible flavoring agent therewithin and an all-enveloping mass of a chewing gum base within which the particles are substantially distributed."

U.S. Pat. No. 3,753,730 issued on Aug. 21, 1973 discloses processes for altering the flavors of particulate grain products comprising applying a composition comprising a flavoring agent, an edible cold water insoluble film former and a vehicle to a particulate grain product; drying the distributed composition to form a flavor containing film on the grain product; and then optionally distributing the coated flavored grain through a large mass of uncoated grain particles.

German Offenlegungsschrift No. 28 26 042 published on Jan. 4, 1979 discloses a condiment consisting of a lemon flavored salt prepared by mixing salt and a lemon oil powder and spaying the resulting mixture with lemon oil. More particularly, the salt is admixed with (a) from 0.1 up to 0.5 weight percent of salt of a terpene-free lemon oil bonded to a powdery carrier and (b) terpene-free liquid lemon oil. The condiment is prepared by mixing the dry salt with component (a), spraying the mixture with component (b) and mixing through a screw conveyor.

Nothing in the prior art discloses the multi-layer sequentially timed release poly-functional volatilizable substance delivery article of my invention.

SUMMARY OF THE INVENTION

My invention covers multi-layer, multi-functional volatilizable substance delivery articles. By the term "multi-functional" is meant perfumery, flavoring, animal repellent, pheromone, insect repellent, insect attractant, air freshener and tobacco flavor. The articles of my invention are constructed in order to deliver, in sequentially timed fashion, to the environment surrounding the article, (e.g., atmosphere or body of water) different fish feed attractants, repellents, combinations thereof, perfumes having different aroma profiles, insect repellents which repel different insects, e.g., *Aedes albopictus* or *Aedes agyptae* or *Musca domestica L* ... during the day time hours and during the night time hours, air freshener-insect repellent combinations, perfume-air freshener combinations and the like. The article can be constructed where one of the layers is, for example, a gel layer and the matrix layer adjacent thereto is composed of perfume containing particles which emit a fragrance in a sustained release function. Thus, for example, the perfume containing particles can be particles shown to be produced in U.S. Pat. No. 4,521,541 issued on Jun. 4, 1985 the specification for which is incorporated herein by ref The gel, for example, may be a gellan gum such KELCOGE ® manufactured and distribute the Kelco Division of Merck & Co., Inc., 8355 Aero Drive, San Diego, Calif.

More specifically, my invention covers a multi-layer sequentially timed release polyfunctional volatilizable substance delivery article comprising a plurality of concentric or coaxial neighboring matrix layers which layers (i) have a finite thickness (e.g., from about 0.5 mm up to about 5 cm) having a finite thickness vector t, and two matrix surfaces each of which is substantially perpendicular to the thickness vector t and (ii) consisting essentially of a suspension agent which is substantially non-flowable at ambient conditions (e.g., a gel or a particulate microporous polymer suspension agent such as microporous polyethylene or microporous polypropylene) containing at least one volatilizable substance capable of emission from a matrix surface (e.g., a perfume composition, a flavor composition, an insect repellent, a pheromone, a deodorant or an air freshener), a surface of one matrix layer being prior to the use of the article contiguous with a surface of its neighboring matrix layer whereby on use of the article the outer most matrix layer initially evolves its contained volatilizable substance at a rate substantially greater than the rate at which its neighboring matrix layer evolves its contained volatilizable substance until such point in time that sufficient volatilizable substance contained in the outer most matrix layer has been evolved into the environment surrounding the article, that a substantial portion of the surface of the neighboring matrix layer is at least constructively exposed to the surrounding environment thereby permitting a substantial increase in the rate of emission of volatilizable substance from the neighboring matrix layer. The term "at least constructively exposed" is intended to mean that the surface is either actually newly exposed as a result of diminishment of the gel as a result of release of the volatilizable substance contained within the gel, for example, or that the micropores of the overlaying matrix on losing all of their volatilizable substance are suddenly able to permit new volatilizable substance to enter and pass therethrough.

More specifically, an embodiment of the multi-layer sequentially timed release polyfunctional volatilizable substance delivery article of my invention comprises:

(a) a first matrix layer (i) having a finite thickness having a finite thickness vector $t_1$, an inner first matrix surface perpendicular to said vector $t_1$ and on outer first matrix surface substantially perpendicular to said vector $t_1$ and (ii) consisting essentially of a first continuous, discontinuous non-particulate or discontinuous particulate solid, semi-solid or gel, porous or non-porous suspension agent containing a first volatilizable substance (e.g., perfume) capable of emission thereof from said outer first matrix surface;

(b) a second matrix layer (i) having a finite thickness vector $t_2$, an inner second matrix surface substantially perpendicular to said vector $t_2$ and an outer second matrix surface substantially perpendicular to said vector $t_2$ and (ii) consisting essentially of a second continuous, discontinuous non-particulate or discontinuous particulate solid, semi-solid or gel porous or non-porous suspension agent containing a second volatilizable substance capable of emission thereof from the inner second matrix surface, said inner second matrix surface being, prior to use of said article, contiguous with said outer first matrix surface whereby on use of said article, said first matrix layer initially evolves said first volatilizable substance at a rate substantially greater than the rate at which said second matrix layer evolves said second volatilizable substance until such point in time that sufficient first volatilizable substance has been evolved into the environment surrounding said article, that a substantial portion of said second inner surface is at least constructively exposed to the surrounding environment thereby permitting a substantial increase in the rate of emission of said second volatilizable substance.

Still another embodiment of the multi-layer sequentially timed release polyfunctional volatilizable substance delivery article of my invention has a vertically disposed "y" axis comprising:

(a) a horizontally disposed first matrix layer having a first upper matrix surface in an "x-z" plane having a maximum variable radius $R_1$ and a first lower matrix surface in an "x-z" plane having a maximum variable ration $R_1'$, said "x-z" planes being perpendicular to said "y" axis, (i) consisting essentially of a first continuous, discontinuous non-particulate or discontinuous particulate solid, semi-solid or gel porous or non-porous suspension agent containing a first volatilizable substance, (e.g., a first perfume) capable of emission from said first upper surface; (ii) having a horizontally disposed first "x-z" matrix median plane having a first circumferential outer boundary located in said first "x-z" matrix median plane; and (iii) having an unbroken first side wall extending both upwardly at a distance $H_1$ and downwardly at a distance $H_1$ from said first circumferential outer boundary, in a direction substantially perpendicular thereto on said "y" axis and a first outer matrix wall surface;

(b) a second horizontally disposed matrix layer coaxial with reference to said "y" axis with said first matrix layer having a second upper matrix surface in an "x-z" plane having a maximum variable radius $R_2$ initially substantially cocircumferential with, contiguous with and substantially coplanar with said first lower matrix surface of said first matrix layer, and a second lower matrix surface in an "x-z" plane having a maximum variable radius $R_2'$ substantially parallel to said second upper matrix surface (i) consisting essentially of a second continuous, discontinuous non-particulate or discontinuous particulate solid, semi-solid or gel porous or non-porous suspension agent having contained therein a second volatilizable substance capable of emission from said upper matrix surface; (ii) having a horizontally disposed second "x-z" matrix median plane having a second circumferential outer boundary located on said second "x-z" matrix median plane, said second "x-z" matrix median plane being substantially parallel to and coaxial with said first "x-z" matrix median plane with reference to said "y" axis; and iii) having an unbroken second side wall extending upwardly at a distance $H_2$ and downwardly at a distance $H_2'$ from said second circumferential outer boundary in a direction substantially perpendicular thereto on said "y" axis; and having a second outer matrix wall surface;

(c) a volatilizable substance-impervious laminar support means for supporting said second matrix layer, said second support means (i) having an upper support surface located in an "x-z" plane having a maximum radius $R_3$ perpendicular to said "y" axis; said upper support surface being initially contiguous with and substantially coplanar with said second lower matrix surface; (ii) having a horizontally disposed "x-z" support median plane having a third circumferential outer boundary located in said "x-z" support median plane; and (iii) having an unbroken volatilizable substance-impervious third sidewall extending upwardly at a distance $H_s$ which is greater than or equal to $H_1+H_1'+H_2'$ from said third circumferential outer boundary said third side wall having an inner surface, said inner surface being initially contiguous with and parallel to said first outer matrix wall surface and said second outer matrix wall surface whereby on use of said article, said first matrix layer evolves first volatilizable substance, (e.g., a first perfume) initially at a rate substantially greater than said second matrix layer, evolves said second volatilizable substance (e.g., a second perfume); radi $R_1$ and $R_1'$ diminish at a rate greater than the rate of diminishment of radii $R_2$ and $R_2'$ thereby enabling the emission, at an increasing rate, of said second volatilizable substance.

Still another embodiment of the multi-layer sequentially timed release polyfunctional volatilizable substance delivery article of my invention has a vertically disposed "y" axis comprising:

(a) a vertically disposed first matrix mass (i) having a first unbroken side wall of length $H_1$ substantially parallel to and circumferential with reference to said "y" axis which side wall has a first outer side wall surface; (ii) having a first upper matrix surface horizontally disposed in an "x-z" plane; (iii) having a first lower matrix surface horizontally disposed in an "x-z" plane each of said "x-z" planes being perpendicular to said "y" axis and parallel to one another; (iv) consisting essentially of a first continuous, discontinuous non-particulate or discontinuous particulate solid, semi-solid porous or non-porous suspension agent containing a first volatilizable substance (e.g., a first insect repellent) capable of emission from said first outer side wall surface; (v) covering said first upper matrix surface and said first lower matrix surface volatilizable substance-impervious permanently-affixed laminae having surfaces in the "x-z" plane coplanar and substantially contiguous with the first upper and lower matrix surfaces;

(b) a vertically disposed second matrix mass coaxial with said first matrix mass (i) having a second unbroken inner side wall initially coterminous with said first unbroken side wall of said first matrix mass having initial length $L_1$, circumferential with respect to said "y" axis, and having its surface contiguous with said first outer side wall surface of said first matrix mass (ii) consisting essentially of a second continuous, discontinuous non-particulate or discontinuous particulate solid, semi-solid porous or non-porous suspension agent containing a second volatilizable substance (e.g., second insect repellent) capable of emission from said outer side wall surface whereby on use of said article, said second matrix mass intially evolves said second volatilizable substance (e.g., second insect repellent) initially at a rate substantially greater than said first matrix mass evolves said first volatilizable substance (e.g., first insect repellent) until such point in time that sufficient second volatilizable substance has been evolved into the environment surrounding said article that a substantially portion of said first outer side wall is at least constructively exposed to the surrounding environment thereby permitting a substantial increase in the rate of emission of said first volatilizable substance.

Still another embodiment of my invention is a concentric multi-layer sequentially timed release polyfunctional volatilizable substance delivery article having a first geometric centroid comprising:

(a) a first matrix mass (i) having a first matrix outer surface the points on which are at a range of distances $R_a$–$R_b$ from said geometric centroid and (ii) consisting essentially of a first continuous, discontinuous non-particulate or discontinuous particulate solid, semi-solid porous or non-porous suspension agent containing a first volatilizable substance (e.g., a first room deodorant) capable of emission from said first matrix outer surface;

(b) a second matrix mass concentric with said first matrix mass (i) having a second matrix inner surface contiguous with said first matrix outer surface (ii) having a thickness in the range of $T_1$–$T_2$ (e.g., from about 0.1 mm up to about 5 cm); (iii) having a second matrix outer surface the points on which are at a range of distances $R_a+T_1$ to $R_b+T_2$ from said geo- metric centroid and (iv) consisting essentially of a second continuous, discontinuous non-particulate or discontinuous particulate solid, semi-solid porous or non-porous suspension agent containing a second volatilizable substance (e.g., second room deodorant) capable of emission from said second matrix outer surface whereby on use of said article said second matrix mass initially evolves said second volatilizable substance at a rate substantially greater than said first matrix mass evolves said first volatilizable substance until such point in time that sufficient second volatilizable substance has been evolved into the environment surrounding said article that a substantial portion of said first outer surface is at least constructively exposed to the surrounding environment thereby permitting a substantial increase in the rate of emission of said first volatilizable substance.

BRIEF DESCRIPTION OF THE DRAWINGS

FIG. 1 is a cut-away side elevation view of a bilayer, bifunctional volatilizable substance delivery article of my invention wherein each layer is in the form of a cylinder with the lower surface of one of the cylinders being contiguous and coplanar with the upper surface of the other cylinder.

FIG. 2 is a cut-away side elevation view of the bilayer, bifunctional volatilizable substance delivery article of FIG. 1 during use thereof.

FIG. 3 is another embodiment of a bilayer, bifunctional volatilizable substance delivery article of my invention prior to use thereof wherein each of the layers is in the form of a cylinder and one cylinder has an outer surface contiguous with the lower surface of the other cylinder.

FIG. 4 is a cut-away side elevation view of the article of FIG. 3 during the operation thereof.

FIG. 5 is a cut-away side elevation view of another embodiment of the bilayer, bifunctional volatilizable substance delivery article of my invention in the form of a cone wherein the lower matrix layer is in the form of a cone having an upper flat surface and the upper matrix layer is in the form of a frustum of a cone with the lower surface of the frustum being contiguous with the upper surface of the lower cone matrix.

FIG. 6 is a cut-away side elevation view of the use of a plurality of articles as depicted in FIG. 5 wherein each of the articles is held in a stand and each of the articles is capable of delivering different volatilizable substances at different times, e.g., insect repellents, perfumes, air fresheners and room deodorants.

FIG. 7 is a cut-away side elevation view of the use of the article of FIG. 5 contained in a heating bath wherein the volatilization of the volatilizable substances contained in the article of FIG. 5 is accelerated as a result of the use of the heating bath.

FIG. 8 is a cut-away perspective view of a concentric multi-layer sequentially timed release bifunctional volatilizable substance delivery article of my invention in the shape of a suspended sphere.

FIG. 9 is a cut-away side elevation view of the concentric bilayer sequentially timed release bifunctional volatilizable substance delivery article of FIG. 8.

FIG. 10 is a perspective view of a bilayer sequentially timed release bifunctional volatilizable substance delivery article which is in the form of two vertically disposed upright concentric cylinders.

FIG. 11 is a cut-away side elevation view of the embodiment of my invention shown in perspective view in FIG. 10 retained in a supporting means wherein the core cylinder is restrained from initial outward emission of the volatilizable substance contained therein.

FIG. 13 is a cut-away side elevation view of the article of FIG. 11 while in use.

FIG. 12 is a top view cf an article of the type illustrated in FIG. 10 with the exception that the article consists of four coaxial concentric cylindrical layers of volatilizable substance.

FIG. 14 sets forth a graph of intensity of perceptible desirable aroma evolved from an article of my invention as illustrated in FIG. 1 versus time for each of the two aromas evolved as a result of the use of fragrances in each of the matrix layers of the article.

DETAILED DESCRIPTION OF THE DRAWINGS

Referring to FIG. 1, a gel layer in the form of a cylinder 19 having lower surface 16 and upper surface 17a contains islands or holes which contain perfume material of a given first formulation 18. The lower layer having upper surface 16 contains microporous polymer particles 14 which have included therein a second perfumery material. Such microporous polymer particle may be produced according to the processes set forth in U.S. Pat. No. 4,521,541 issued on Jun. 4, 1985 the specification for which is incorporated by reference herein. The cylinders are supported in container 12 having inner wall 21 and cover 23. When not in use the cover 23 is in a closed position supported on the wall 12. Prior to use, the two cylinders have side walls that abut and are contiguous with inner wall surface 21. The overall article 10 when in use is shown in use in FIG. 2. The gel layer having surface 17a is reduced in its lateral and longitudinal dimensions and is shown in FIG. 2 to have lateral surface 17b and longitudinal surface 17c. The fragrance evolving into the environment in FIG. 2 is coming from both the gel layer and the particulate lower layer into environment 24. The evolution of fragrance is shown by reference numeral 25.

FIG. 3 shows the use of two gel layers 34 and 38 in a bilayer cylindrical mode 30. Prior to use, both layers 34 and 38 which have a common surface 36 abut inner wall 31 in cylinder 32. The upper surface 37a is the one from which fragrance or other volatilizable substance is initially evolved as shown in FIG. 4. Cover 43 is in a closed position when the article 30 is not in use.

FIG. 4 shows the article of FIG. 3 when in use showing the reduction in dimensions of cylinders 34 and 38 and showing that cylinder 38 has been reduced to a much greater extent than cylinder 34 thereby permitting fragrance to be evolved not only from cylinder 38 but also from cylinder 34. The surfaces of cylinder 38 on use are shown as 37b (lateral) and 37c (longitudinal). The fragrance is evolved from both cylinders 34 and 38 and the evolution of the fragrances shown by reference numeral 34 into surrounding atmosphere 44.

With reference to FIG. 5, the cut-away side elevation view of the cone containing two volatilizable substance-containing matrices, the lower layer, the conical layer 54 is held in position in cone 52. The upper surface of the particulate layer 54 containing particles, for example, those defined according to the disclosure of U.S. Pat. No. 4,521,541 issued on Jun. 4, 1985 has its upper surface 56 contiguous with the lower surface of the upper layer 58 which is in the shape of a frustum of a cone. The foam 58 contains perfume materials 59 disbursed therein which are evolved from surface 57a initially on use of the article 50 of FIG. 5. When the article 50 is not in use cover 53 is in position on side wall 52. When cover 53 is opened, the article is in use and the initial fragrance or other volatilizable substance evolves from surface 58a from the foam or gel 58. As the article is being used, the foam layer 58 or gel layer 58 shrinks away from the inner wall of cone 52, that is, shrinks away from the inner surface 51. When the gel or foam shrinks away from wall 51 it starts leaving surface 56 exposed; that is, the upper surface of the cone 54. When the upper surface 56 of cone 54 is exposed fragrance or other volatilizable substance, e.g., air freshener is evolved from cone 54 as it is evolved to a lesser extent from frustum of cone 58.

The operation of the article of FIG. 5, that is article 50 is shown in FIG. 7 when such a cone 52 is heated using, for example, hot oil 73 contained in heating article 70. The hot oil is contained in container 71 and is heated by heating unit 75. Vent holes 76 permit any vapors from the hot oil to be evolved into the outer atmosphere together with perfume from article 50 which is held in place in orifice 72 of article 70. The hot air venting from container 71 is indicated by reference numeral 77. The venting of the fragrance from cone 50 into the atmosphere surrounding the cone is indicated by reference numeral 78.

FIG. 6 shows another use of a plurality of the cones shown in FIG. 5 as articles 50a, 50b, 50c and 50d. Each of the cones can evolve different fragrances at different times as a result of different porosities of foam or gel 58 (shown in FIG. 5). On use of the articles (which may be used in seriatum) the covers can be pulled up causing surface 57a of FIG. 5 to be exposed at different points in time. Each of articles 50a, 50b, 50c and 50d may be held in place in openings 62a, 62b, 62c and 62d of the platform 61 of the unit 60 of FIG. 6.

Another embodiment of my invention is a bilayer spherical article shown in partially cut-away perspective view in FIG. 8 and shown in cut-away side elevation view in FIG. 9. Inner layer 81 is made up of a ball of particles such as those defined in U.S. Pat. No. 4,521,541 issued on Jun. 4, 1985. The outer layer 82 may be a gel containing either perfume or air freshener particles 83. The entire article 80 is suspended from hanging wire 85 using support disk 84. The hanging wire 85 may have a flanged support 87 interwoven in the ball of particles 81, with the flange support being indicated by reference numeral 87. The outer gel may be a gel such as that set forth and described in Example I, infra, and in United Kingdom Specification No. 1,598,449 published on Sep. 23, 1981, the specification of which is incorporated by reference herein or U.S. Pat. No. 2,465,470 the specification of which is incorporated by reference herein. As the outer layer gel 82 or foam 82 is used up; that is, as perfume 83 is evolved, pores are open in layer 82 to permit fragrance or air freshener from particles 81 to be evolved into the atmosphere surrounding article 80 until finally only volatilizable substance from core 81 is evolved from article 80 (at that point in time when volatilizable substance 83 is completely dissipated from layer 82.

Article 100 shown in FIG. 10 and shown in use in FIG. 11 has a solid lid on its central cylindrical core 103 made up of pellets as defined in U.S. Pat. No. 4,521,541. The surface of these pellets 105 has cover 104 held in place by wire restrainer 108 which is attached to the cylinder wall 109 of article 110. The surface of the outer cylinder 106 which is a cylinder containing foam or gel 101 containing perfume or air freshener or insect repellent particles 107 is the first surface from which volatilizable substance is evolved into the atmosphere While in use the article of FIG. 10, article 100 is shown in use in FIG. 13. As foam or gel 101 is dissipated, the surface of the inner core cylinder 103 becomes exposed thereby permitting fragrance or air freshener or insect repellent or the like to be evolved from the central core cylinder 103 into the atmosphere in addition to the volatilizable substance being evolved from the gel or foam 101 as shown in FIG. 13. Another embodiment is shown, in top view, wherein four layers of sequentially timed release quadri-functional volatilizable substances are delivered to the atmosphere sequentially. Thus, for example, pellets as defined in U.S. Pat. No. 4,521,541 of Jun. 4, 1985 may be contained in core cylinder 125 and in the third concentric cylinder 122. The second concentric cylinder 123 and the outer concentric cylinder 121 may be composed of gel or foam containing perfume, air freshener or insect repellent substances therein. Thus, foam or gel layers 123 and 121 concentric with layers 122 and central layer 125 may be composed of a gel as defined in U.K. Specification 1,598,449 published on Sep. 23, 1981 or U.S. Pat. No. 2,465,470 or U.S. Pat. No. 2,691,615 or U.S. Pat. No. 2,927,055 the specifications for which are incorporated herein by reference.

Thus, lids can be held by retaining wires on the upper flat surface of inner core cylinder 125, on the second concentric cylinder 123 and on the third concentric cylinder 122. Thus, the only volatilizable substance that can be evolved would be evolved from outer cylinder 121. As the outer cylinder gel or foam 121 evolves its fragrance 126 into the outer atmosphere 129 from surface 128 (with fragrance or other volatilizable substance being evolved shown by reference numeral 130; that is, being evolved from article 120), the outer surface of third cylinder 122 becomes exposed to the atmosphere and volatilizable substance or fragrance is then capable of being evolved from concentric cylinder 122 into the atmosphere along with fragrance from outer cylinder 121. As volatilizable substance from concentric cylinder 122 is used up, surface of cylinder 123 becomes exposed and volatilizable substance from cylinder 123 is then evolved into the atmosphere. Then, as fragrance or other volatilizable substance on use is evolved from cylinder 123, volatilizable substance from cylinder 125 is finally capable of being evolved into the atmosphere. The nature of each of the concentric cylinders may be such that the timing of evolution of volatilizable substance from each of the concentric cylinders may be easily timed.

Thus, referring to FIG. 14, the intensity of perceptible desirable aroma, for example, being evolved from the article 10 of FIG. 1 (having two cylindrical layers) is shown by the two graphs indicated as "Aroma $A_1$ and "Aroma $A_2$". At time zero, only aroma "Aroma $A_1$" is evolved as time proceeds to time $t_1$, evolution of "Aroma $A_2$" commences and goes up to a maximum shortly after time $t_1$ and then it too is dissipated by time $t_2$ as shown in FIG. 14.

EXAMPLES I-VII

Air-treating gels were prepared having the compositions described in the table.

TABLE

| Components | EXAMPLES | | | | | | |
|---|---|---|---|---|---|---|---|
| | I | II | III | IV | V | VI | VII |
| Sodium stearate | 20 | 15 | 15 | 15 | 10 | 10 | 15 |
| Monoethyl ether of diethylene glycol | 55 | 65 | 50 | 55 | 65 | 60 | — |
| Monoethyl ether of triethylene glycol | — | — | — | — | — | — | 50 |
| Water (distilled) | 5 | — | 15 | 20 | 10 | — | 15 |
| Perfume (EVERFRESH ®) | 20 | 20 | 20 | 10 | 15 | 30 | 20. |

Into a one liter cylindrical vessel as shown in FIGS. 1 and 2 and described in the Detailed Description of The Drawings, supra, polyethylene foamed particles prepared according to the procedure set forth at column 12, lines 24–67 and column 13, lines 1–21 of U.S. Pat. No. 4,521,541 issued on Jun. 4, 1985 are added to the cylinder until the cylinder having an internal radius of 10 cm contains 100 grams of particles each having a diameter of 0.1 cm. The particles are arranged so that the upper surface thereof, surface 16 in FIG. 1 is substantially planar. Surface 16 is then covered with 200 grams of gel per each of Examples I, II, III, IV, V, VI and VII. The perfume contained in each of the polyethylene particles is a rose perfume containing the following formulation:

| | |
|---|---|
| Phenylethyl alcohol | 30 parts |
| Rose oxide | 22 parts |
| Beta-Ionone | 15 parts |
| Trans,trans-delta-damascone | 42 parts. |

The gel of layer 18 containing the EVERFRESH ® perfume is prepared by any convenient technique such as by mixing the components and refluxing the mixture with stirring for 10 to b 60 minutes at a temperature of from 80° to 110° C. until the soap completely dissolves.

A gel forms upon the cooling of the mixture and the mixture at that point in time is poured onto the particles of polyethylene containing rose perfume.

In each instance the atmosphere surrounding article 10 when cover 23 is initially that of the EVER-FRESH ® perfume air freshener. As gel 18 shrinks on useage, the rose fragrance from layer 14 evolves from surface 16 into the atmosphere 24 (shown in FIG. 2). It should be noted that the gels remained rigid at temperatures of up to at least 55° C.

What is claimed is:

1. A multi-layer sequentially timed release polyfunctional volatilizable substance delivery article comprising a plurality of concentric or coaxial neighboring matrix layers, said layers
   (i) having a finite thickness having a finite thickness vector t and two matrix surfaces each of which is substantially perpendicular to said thickness vector t; and
   (ii) consisting essentially of a suspension agent which is substantially non-flowable at ambient conditions containing at least one volatilizable substance capable of emission from a matrix surface, a surface of one matrix layer being, prior to use of said article, contiguous with a surface of its neighboring matrix layer, whereby on use of said article, the outermost matrix layer initially evolves its contained volatilizable substance at a rate substantially greater than the rate at which its neighboring matrix layer evolves its contained volatilizable substance until such point in time that sufficient volatilizable substance contained in the outermost matrix layer has been evolved into the environment surrounding said article, that a substantial portion of the surface of the neighboring matrix layer is at least constructively exposed to the surrounding environment thereby permitting a substantial increase in the rate of emission of volatilizable substance from the neighboring matrix layer.

2. The multi-layer sequentially timed release polyfunctional volatilizable substance delivery article of claim 1 comprising:
   (a) a first matrix layer
      (i) having a finite thickness having a finite thickness vector $t_1$, an inner first matrix surface substantially perpendicular to said vector $t_1$ and an outer first matrix surface substantially perpendicular to said vector $t_1$; and
      (ii) consisting essentially of a first continuous, discontinuous non-particulate or discontinuous non-porous suspension agent containing a first volatilizable substance capable of emission thereof from said outer first matrix surface;
   (b) a second matrix layer
      (i) having a finite thickness having a finite thickness vector $t_2$, an inner second matrix surface substantially perpendicular to said vector $t_2$ and an outer second matrix surface substantially perpendicular to said vector $t_2$; and
      (ii) consisting essentially of a second continuous, discontinuous non-particulate or discontinuous particulate solid, semi-solid or gel porous or non-porous suspension agent containing a second volatilizable substance capable of emission thereof from said inner second matrix surface, said inner second matrix surface being, prior to use of said article, contiguous with said outer first matrix surface whereby on use of said article said first matrix layer initially evolves said first volatilizable substance at a rate substantially greater than the rate at which said second matrix layer evolves said second volatilizable substance until such point in time that sufficient first volatilizable substance has been evolved into the environment surrounding said article, that a substantial portion of said second inner surface is at least constructively exposed to the surrounding environment thereby permitting a substantial increase in the rate of emission of said second volatilizable substance.

3. The multi-layer sequentially timed release polyfunctional volatilizable substance delivery article of claim 1 having a vertically disposed "y" axis comprising:
   (a) a horizontally disposed first matrix layer having a first upper matrix surface in a "x-z" plane having a maximum variable radius $R_1$ and a first lower matrix surface in an "x-z" plane having a maximum variable radius $R_1'$, said "x-z" planes being perpendicular to said "y" axis;
      (i) consisting essentially of a first continuous, discontinuous non-particulate or discontinuous particulate solid, semi-solid or gel porous or non-porous suspension agent containing a first volatilizable substance capable of emission from said first upper surface;
      (ii) having a horizontally disposed first "x-z" matrix median plane having a first circumferential outer boundary located in said first "x-z" matrix median plane; and
      (iii) having an unbroken first side wall extending both upwardly at a distance $H_1$ and downwardly at a distance $H_1'$ from said first circumferential outer boundary in a direction substantially perpendicularly thereto on said "y" axis, and a first outer matrix wall surface;
   (b) a second horizontally disposed matrix layer coaxial with reference to said "y" axis with said first matrix layer having a second upper matrix surface in an "x-z" substantially co-circumferential with, contiguous with and substantially coplanar with said first lower matrix surface of said first matrix layer, and a second lower matrix surface in an "x-z" plane having a maximum variable radius $R_2'$ substantially parallel to said second upper matrix surface
      (i) consisting essentially of a second continuous, discontinuous non-particulate or discontinuous particulate solid, semi-solid or gel porous or non-porous suspension agent having contained therein a second volatilizable substance capable of emission from said second upper matrix surface;
      (ii) having a horizontally disposed second "x-z" matrix median plane having a second circumferential outer boundary located in said second "x-z" matrix median plane, said second "x-z" matrix median plane being substantially parallel to and coaxial with said first "x-z" matrix median plane with reference to said "y" axis; and
      (iii) having an unbroken second side wall extending upwardly at a distance $H_2$ and downwardly at a distance $H_2'$ from said second circumferential outer boundary in a direction substantially perpendicular thereto on said "y" axis; and having a second outer matrix wall surface;

(c) a volatilizable substance-impervious laminar support means for supporting said second matrix layer, said support means
  (i) having an upper support surface located in an "x-z" plane having a maximum radius $R_3$ perpendicular to said "y" axis; said upper support surface being initially contiguous with and substantially coplanar with said second lower matrix surface;
  (ii) having a horizontally disposed "x-z" support median plane having a third circumferential outer boundary located in said "x-z" support median plane; and
  (iii) having an unbroken volatilizable substance-impervious third side wall extending upwardly at a distance $H_s$ which is greater than or equal to $H_1+H_1'+H_2+H_2'$ from said third circumferential outer boundary, said third side wall having an inner surface, said inner surface being initially contiguous with and parallel to said first outer matrix wall surface and said second outer matrix wall surface, whereby on use of said article, said first matrix layer evolves first volatilizable substance initially at a rate substantially greater than said second matrix layer evolves said second volatilizable substance; radii $R_1$ and $R_1'$ diminish at a rate greater than the rate of diminishment of radii $R_2$ and $R_2'$ thereby enabling the emission at an increasing rate of said second volatilizable substance.

4. The multi-layer sequentially timed release polyfunctional volatilizable substance delivery article of claim 1 having a vertically disposed "y" axis comprising:
  (a) a vertically disposed first matrix mass
    (i) having a first unbroken side wall of length $H_1$ substantially parallel to and circumferential with reference to said "y" axis which side wall has a first outer side wall surface;
    (ii) having a first upper matrix surface horizontally disposed in an "x-y" plane;
    (iii) having a first lower matrix surface horizontally disposed in an "x-y" plane, each of said "x-y" planes being perpendicular to said "y" axis and parallel to one another;
    (iv) consisting essentially of a first continuous, discontinuous non-particulate or discontinuous particulate solid, semi-solid porous or non-porous suspension agent containing a first volatilizable substance capable of emission from said outer side wall surface;
    (v) covering said first upper matrix surface and said first lower matrix surface, volatilizable substance-impervious permanently affixed laminae having surfaces in the "x-z" plane coplanar and substantially contiguous with the first upper and lower matrix surfaces;
  (b) a vertically disposed second matrix mass coaxial with said first matrix mass;
    (i) having a second unbroken inner side wall initially coterminous with said first unbroken side wall of said first matrix mass having an initial length $L_1$, circumferential with reference to said "y" axis, and having its surface contiguous with said first outer side wall surface of said first matrix mass; and
    (ii) consisting essentially of a second continuous, discontinuous non-particulate or discontinuous particulate solid, semi-solid porous or non-porous suspension agent containing a second volatilizable substance capable of emission from said second outer side wall surface, whereby on use of said article, said second matrix mass initially evolves said second volatilizable substance initially at a rate substantially greater than said first matrix mass evolves said first volatilizable substance until such point in time that sufficient second volatilizable substance has been evolved into the environment surrounding said article that a substantial portion of said first outer side wall is at least constructively exposed to the surrounding environment thereby permitting a substantial increase in the rate of emission of said first volatilizable substance.

5. A concentric multi-layer sequentially timed release polyfunctional volatilizable substance delivery article of claim 1 having a fixed geometric centroid comprising:
  (a) a first matrix mass
    (i) having a first matrix outer surface, the points on which are at a range of distances $R_a-R_b$ from said geometric centroid; and
    (ii) consisting essentially of a first continuous, discontinuous non-particulate or discontinuous particulate solid, semi-solid, porous or non-porous suspension agent containing a first volatilizable substance capable of emission from said first matrix outer surface;
  (b) a second matrix mass concentric with said first matrix mass
    (i) having a second matrix inner surface contiguous with said first matrix outer surface;
    (ii) having a thickness range of $T_1-T_2$;
    (iii) having a second matrix outer surface the points on which are at a range of distances $R_a+T_1$ to $R_b+T_2$ from said geometric centroid; and
    (iv) consisting essentially of a second continuous, discontinuous non-particulate or discontinuous particulate solid, semi-solid, porous or non-porous suspension agent containing a second volatilizable substance capable of emission from said second matrix outer surface, whereby on use of said article said second matrix mass initially evolves said second volatilizable substance at a rate substantially greater than said first matrix mass evolves said first volatilizable substance until such point in time that sufficient second volatilizable substance has been evolved into the environment surrounding said article that a substantial portion of said first outer surface is at least constructively exposed to the surrounding environment thereby permitting a substantial increase in the rate of emission of said first volatilizable substance.

* * * * *